United States Patent
Petersen et al.

(10) Patent No.: US 8,750,954 B2
(45) Date of Patent: Jun. 10, 2014

(54) MEDICAL MONITORING PATCH DEVICE AND METHODS

(75) Inventors: Ethan Petersen, Oakland, CA (US); Mark Perez, Denair, CA (US)

(73) Assignee: Covidien LP, Manfield, MA (US)

( * ) Notice: Subject to any disclaimer, the term of this patent is extended or adjusted under 35 U.S.C. 154(b) by 716 days.

(21) Appl. No.: 12/935,747

(22) PCT Filed: Mar. 31, 2009

(86) PCT No.: PCT/US2009/039002
§ 371 (c)(1),
(2), (4) Date: Sep. 30, 2010

(87) PCT Pub. No.: WO2009/124076
PCT Pub. Date: Oct. 8, 2009

(65) Prior Publication Data
US 2011/0028814 A1      Feb. 3, 2011

Related U.S. Application Data

(60) Provisional application No. 61/072,600, filed on Mar. 31, 2008.

(51) Int. Cl.
*A61B 5/1455* (2006.01)

(52) U.S. Cl.
USPC ............... 600/323; 600/344; 600/324

(58) Field of Classification Search
USPC ................................. 600/309–344
See application file for complete search history.

(56) References Cited

U.S. PATENT DOCUMENTS

| | | | |
|---|---|---|---|
| 5,090,410 A * | 2/1992 | Saper et al. ............ | 602/41 |
| 5,477,853 A | 12/1995 | Farkas | |
| 5,645,059 A | 7/1997 | Fein | |
| 5,995,859 A * | 11/1999 | Takahashi ............ | 600/323 |
| 6,825,619 B2 | 11/2004 | Norris | |
| 6,954,664 B2 | 10/2005 | Sweitzer | |
| 7,048,687 B1 | 5/2006 | Reuss et al. | |
| 7,085,597 B2 | 8/2006 | Fein et al. | |
| 7,120,479 B2 | 10/2006 | Chew | |
| 7,120,480 B2 | 10/2006 | Chew | |
| 7,215,985 B2 | 5/2007 | Petersen | |
| 7,272,425 B2 | 9/2007 | Al-Ali et al. | |

(Continued)

FOREIGN PATENT DOCUMENTS

DE   69123448   5/1997
EP   0194105 A2   9/1986

(Continued)

OTHER PUBLICATIONS

International Search Report and Written Opinion mailed Jun. 29, 2009 for PCT/US2009/039002.

(Continued)

*Primary Examiner* — Eric Winakur
*Assistant Examiner* — Marjan Fardanesh
(74) *Attorney, Agent, or Firm* — Fletcher Yoder PC (57) ABSTRACT

Embodiments described herein may include systems and methods for monitoring physiological parameters of a patient. Specifically, embodiments disclose the use of a generally self-contained pulse oximeter that is small and lightweight, such that it may be comfortably affixed to a patient to provide physiological data pertaining to the patient. Embodiments also provide methods of using and manufacturing a pulse oximetry patch.

17 Claims, 4 Drawing Sheets

(56) References Cited

U.S. PATENT DOCUMENTS

| | | |
|---|---|---|
| 7,392,074 B2 | 6/2008 | Isaacson et al. |
| 7,423,526 B2 | 9/2008 | Despotis |
| 7,457,652 B2 | 11/2008 | Porges et al. |
| 2005/0038348 A1* | 2/2005 | Avicola et al. ............. 600/502 |
| 2005/0070773 A1 | 3/2005 | Chin et al. |
| 2005/0101848 A1 | 5/2005 | Al-Ali |
| 2005/0228244 A1 | 10/2005 | Banet |
| 2006/0025660 A1 | 2/2006 | Swedlow et al. |
| 2006/0030762 A1 | 2/2006 | David et al. |
| 2006/0030764 A1 | 2/2006 | Porges et al. |
| 2006/0030765 A1 | 2/2006 | Swedlow et al. |
| 2006/0161054 A1 | 7/2006 | Reuss et al. |
| 2006/0167351 A1 | 7/2006 | Isaacson et al. |
| 2006/0189859 A1 | 8/2006 | Kiani |
| 2006/0200018 A1 | 9/2006 | Al-Ali |
| 2006/0211922 A1 | 9/2006 | Al-Ali |
| 2006/0211923 A1 | 9/2006 | Al-Ali |
| 2006/0211924 A1 | 9/2006 | Smith |
| 2006/0217604 A1 | 9/2006 | Fein et al. |
| 2006/0217605 A1 | 9/2006 | Fein et al. |
| 2006/0217606 A1 | 9/2006 | Fein et al. |
| 2006/0217607 A1 | 9/2006 | Fein et al. |
| 2006/0217608 A1 | 9/2006 | Fein et al. |
| 2006/0224059 A1 | 10/2006 | Swedlow et al. |
| 2006/0229509 A1 | 10/2006 | Al-Ali |
| 2006/0229510 A1 | 10/2006 | Fein et al. |
| 2006/0229511 A1 | 10/2006 | Fein et al. |
| 2006/0241363 A1 | 10/2006 | Al-Ali |
| 2006/0264720 A1 | 11/2006 | Chew |
| 2007/0043269 A1 | 2/2007 | Mannheimer et al. |
| 2007/0043270 A1 | 2/2007 | Mannheimer et al. |
| 2007/0043271 A1 | 2/2007 | Mannheimer et al. |
| 2007/0043272 A1 | 2/2007 | Mannheimer et al. |
| 2007/0043273 A1 | 2/2007 | Mannheimer et al. |
| 2007/0043274 A1 | 2/2007 | Mannheimer et al. |
| 2007/0043275 A1 | 2/2007 | Mannheimer et al. |
| 2007/0043276 A1 | 2/2007 | Mannheimer et al. |
| 2007/0043277 A1 | 2/2007 | Mannheimer et al. |
| 2007/0043278 A1 | 2/2007 | Mannheimer et al. |
| 2007/0043279 A1 | 2/2007 | Mannheimer et al. |
| 2007/0043280 A1 | 2/2007 | Mannheimer et al. |
| 2007/0043282 A1 | 2/2007 | Mannheimer et al. |
| 2007/0049810 A1 | 3/2007 | Mannheimer et al. |
| 2007/0073116 A1 | 3/2007 | Kiani et al. |
| 2007/0078311 A1 | 4/2007 | Al-Ali |
| 2007/0088207 A1 | 4/2007 | Mannheimer et al. |
| 2007/0100219 A1 | 5/2007 | Sweitzer et al. |
| 2007/0112260 A1 | 5/2007 | Diab |
| 2007/0123756 A1 | 5/2007 | Kitajima et al. |
| 2007/0129622 A1 | 6/2007 | Bourget et al. |
| 2007/0290869 A1* | 12/2007 | Debord et al. ............. 340/585 |
| 2008/0030346 A1 | 2/2008 | Despotis |
| 2008/0088467 A1 | 4/2008 | Al-Ali et al. |
| 2008/0287757 A1 | 11/2008 | Berson et al. |
| 2009/0167205 A1 | 7/2009 | Petersen |

FOREIGN PATENT DOCUMENTS

| | | |
|---|---|---|
| JP | 26075354 A | 3/2006 |
| JP | 26271815 A | 10/2006 |
| JP | 26320731 A | 11/2006 |
| JP | 26320732 A | 11/2006 |
| JP | 26325766 A | 12/2006 |
| JP | 27117641 A | 5/2007 |
| JP | 27190122 A | 8/2007 |
| JP | 27330708 A | 12/2007 |
| WO | WO2004078028 A2 | 9/2004 |
| WO | WO2006005169 A1 | 1/2006 |
| WO | WO2007086856 A1 | 8/2007 |
| WO | WO2009124076 A1 | 10/2009 |

OTHER PUBLICATIONS

Active Matrix ePaper Displays; Innovating Display Solutions; SiPix.
Electronic Paper Displays; E Ink Corporation; 2005.
First-Generation Electronic Paper Display from Phlips, Sony and E Ink to be Used in New Electronic Reading Devices; E Ink Corporation; 2005.
Plastic Logic;http://www.plasticlogic.com/product.html ; 2000.
Segmented ePaper Displays; Innovating Display Solutions; SiPix;.

* cited by examiner

MEDICAL MONITORING PATCH DEVICE AND METHODS

BACKGROUND

The present disclosure relates generally to medical devices and, more particularly, to medical monitoring devices.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient.

Pulse oximeters typically utilize a non-invasive sensor that is placed on or against a patient's tissue that is well perfused with blood, such as a patient's finger, toe, forehead or earlobe. The pulse oximeter sensor emits light and photoelectrically senses the absorption and/or scattering of the light after passage through the perfused tissue. The data collected by the sensor may then be used to calculate one or more of the above physiological characteristics based upon the absorption or scattering of the light. More specifically, the emitted light is typically selected to be of one or more wavelengths that are absorbed or scattered in an amount related to the presence of oxygenated versus de-oxygenated hemoglobin in the blood. The amount of light absorbed and/or scattered may then be used to estimate the amount of the oxygen in the tissue using various algorithms.

Pulse oximeters and other medical devices are typically mounted on stands that are positioned around a patient's bed or around an operating room table. When a caregiver desires to command the medical device (e.g., program, configure, and so-forth), the caregiver may manipulate controls or push buttons on the monitoring device itself. The monitoring device typically provides results or responses to commands on a Liquid Crystal Display ("LCD") screen mounted in an externally visible position on the medical device. Patient data, alerts, and other information may be displayed on the monitor directly, or may be transmitted to a central computer monitored by caregivers.

This conventional configuration, however, may have several disadvantages, particularly in emergency situations which may occur remotely from a hospital or medical environment. For example, conventional monitors are too heavy and bulky to be worn or constantly moved around to follow a patient. Additionally, in emergency situations, a convenient power supply may not be readily available, and the time required to set up the monitoring system may not be available considering other pressing emergency needs of the patient. The lack of time or a convenient power source may be particularly problematic in large scale emergencies wherein several patients require prompt medical treatment from limited medical personnel working with limited resources. Additionally, the bulk and expense of conventional monitors may make it logistically and economically unfeasible to have large numbers of such monitors on-hand and ready to be transported to emergency sites. It may be desirable, therefore, to have a pulse oximeter that is small, lightweight, inexpensive and battery operated, such that it can be worn by a patient and possibly disposed of after a single use.

SUMMARY

Certain aspects commensurate in scope with the original claims are set forth below. It should be understood that these aspects are presented merely to provide the reader with a brief summary of certain embodiments and that these aspects are not intended to limit the scope of the claims. Indeed, the claims and disclosure may encompass a variety of aspects that may not be set forth below.

Some embodiments described herein are directed to a wholly contained pulse oximetry system that may be worn by a patient. Certain embodiments may include an upper layer that includes a display, a bottom layer that includes one or more light emitters and one or more light detectors for acquiring physiological data from a patient and a middle layer between the upper layer and lower layer that holds the circuitry of the pulse oximetry system, including sensor circuitry, parameter processing circuitry, and display circuitry.

Other embodiments described herein are directed to methods of generating physiological data by a pulse oximetry system that is worn by a patient in the form of a patch for example. The pulse oximetry system may perform the acts of: driving LEDs to emit a light signal into a tissue to be tested; receiving a modified light signal after it has been transmitted through or reflected from the tissue to be tested; generating a physiological parameter based on the modified light signal; and generating a display output of the physiological parameter on an outer surface of the patch.

Other embodiments described herein are directed to methods of monitoring a patient by affixing a wholly contained pulse oximeter to the tissue of a patient and observing a physiological data display included on the pulse oximeter.

Still other embodiments described herein are directed to a method of manufacturing a pulse oximeter, such as by providing pulse oximeter circuitry configured to sense, process, and display physiological data of a patient, and enclosing the pulse oximeter circuitry within an enclosure configured to be disposed adjacent to a tissue of the patient.

BRIEF DESCRIPTION OF THE DRAWINGS

Advantages of the disclosure may become apparent upon reading the following detailed description and upon reference to the drawings in which.

DETAILED DESCRIPTION

One or more embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Certain embodiments relate to a wholly contained pulse oximetry system that is small and lightweight such that it can be worn by a patient. Such a pulse oximetry system may be a small, battery operated, flexible patch that may be adhesively or otherwise affixed to a patient. Such a patch may be used once and thrown away. Therefore, such a pulse oximetry patch may be constructed inexpensively, having very simplified features and displays compared to a traditional pulse oximetry system.

Figure 1A:
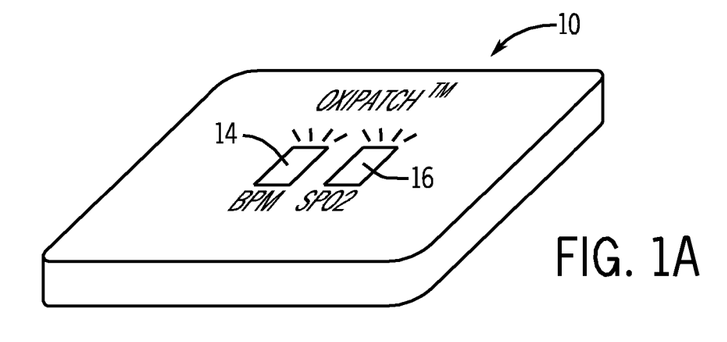
FIG. 1A is a perspective view of a pulse oximetry patch in accordance with an embodiment in which the display includes a pair of light emitting diodes (LEDs)

FIG. 1A is a perspective view of a front side of pulse oximetry patch 10 in accordance with an embodiment. The front side of the pulse oximetry patch 10 is the side that would be visible to a caregiver after the pulse oximetry patch 10 is affixed to a patient. The pulse oximetry patch 10 may be small enough to be affixed to a patient and also holds circuitry utilized for sensing, processing and displaying physiological data of a patient. Because the pulse oximetry patch 10 is to be affixed to a patient, it will typically be small and lightweight. For example, it may have a surface area in the range of approximately three or four square inches, and a thickness in the range of one-eighth of an inch. Additionally, to provide for a secure and comfortable fit, the patch 10 may be flexible. Furthermore, the patch 10 may also include various textual printing on the outer surface, such as, for example, labels, use instructions and model information. As will be explained in more detail below, the patch 10 may be made of any material known in the art such as, for example, polymeric materials.

The pulse oximetry patch 10 may also include a display, illustrated here as two displays 14 and 16, which display certain physiological data of a patient. The displays 14 and 16 may display any data that is useful to a caregiver monitoring a patient. As example, the display 14 may include an LED that blinks correlatively with the heart beat of the patient. For another example, the display 16 may be activated or deactivated in response to the blood-oxygen saturation level of a patient. Specifically, in some embodiments the display 16 may light up when the patient's blood-oxygen level is above acceptable levels, informing the caregiver that the patient's blood-oxygen level is normal. In alternate embodiments, the display 16 may light up when the patient's blood-oxygen level is below acceptable levels, alerting the caregiver that the patient's blood-oxygen level is too low. Furthermore, the displays 14 and 16 may be color coded. For example, the display 16 may include an LED that emits green light when blood-oxygen levels are normal and emits red light when blood-oxygen levels are too low.

Figure 1B:
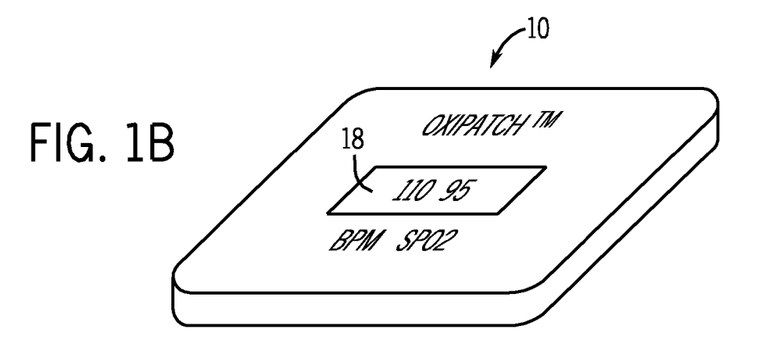
FIG. 1B is a perspective view of a pulse oximetry patch in accordance with an embodiment in which the display includes a numerical display.

Referring to FIG. 1B, an embodiment that includes a numerical display 18 is shown. The numerical display 18 may be configured to display any useful numerical data corresponding to a physiological parameter of a patient, such as, for example, a pulse rate and/or a blood-oxygen saturation level. Additionally, the numerical display 18 may be configured to display data corresponding to the pulse oximetry patch 10 itself, such as, for example, battery life and/or whether the patch 10 is transmitting a wireless signal. Furthermore, the display 18 may be configured to cycle through a set of numerical data, either on a timed basis or responsive to an input of the user.

Figure 2:
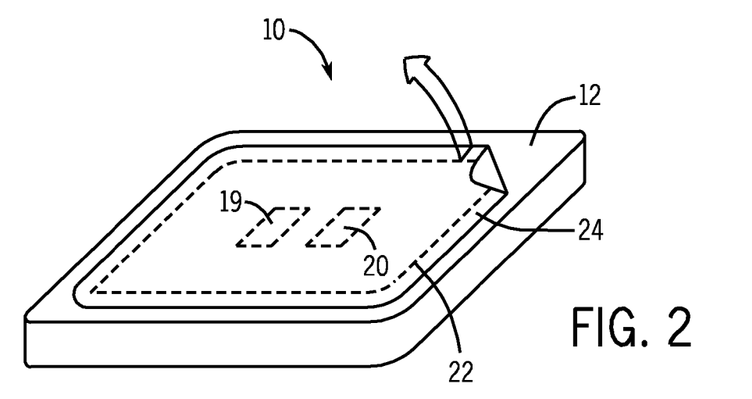
FIG. 2 is a perspective view of the back side of the pulse oximetry patch of FIG. 1A or 1B in accordance with an embodiment.

Referring to FIG. 2, one example of the back side of the pulse oximetry patch 10 is shown. The back side 12 of the pulse oximetry patch 10 is the side that is affixed adjacent to the tissue of a patient. As will be explained further below, the pulse oximetry patch 10 detects physiological data of a patient through sensor circuitry that may include an emitter 19 and a detector 20. The emitter 19 may include one or more LEDs, such as a red LED and an infra-red LED. The detector 20 may be, for example, any kind of photosensor known in the art, such as, for example a photodiode. When operable, both the emitter 19 and detector 20 are in contact with the skin or tissue of a patient.

To hold the pulse oximetry patch 10 against the patient, the back side 12 of the patch 10 may include an adhesive 22 that is configured to hold the pulse oximetry patch 10 against the skin of a patient. Additionally, to protect the adhesive 22 while the pulse oximetry patch 10 is not in use, a protective sheet 24 may be disposed over the adhesive 22. The protective sheet 24 may be configured to be removed just prior to the pulse oximetry patch 10 being affixed to the skin of a patient.

The pulse oximetry patch 10 may be disposed adjacent to any part of a patient's body that is conducive to measuring physiological parameters and that can support the pulse oximetry patch 10, such as for example, the forehead or the wrist. It should also be noted that the pulse oximetry patch 10 may be calibrated for use over a particular bodily area or tissue measurement site.

Figure 3:
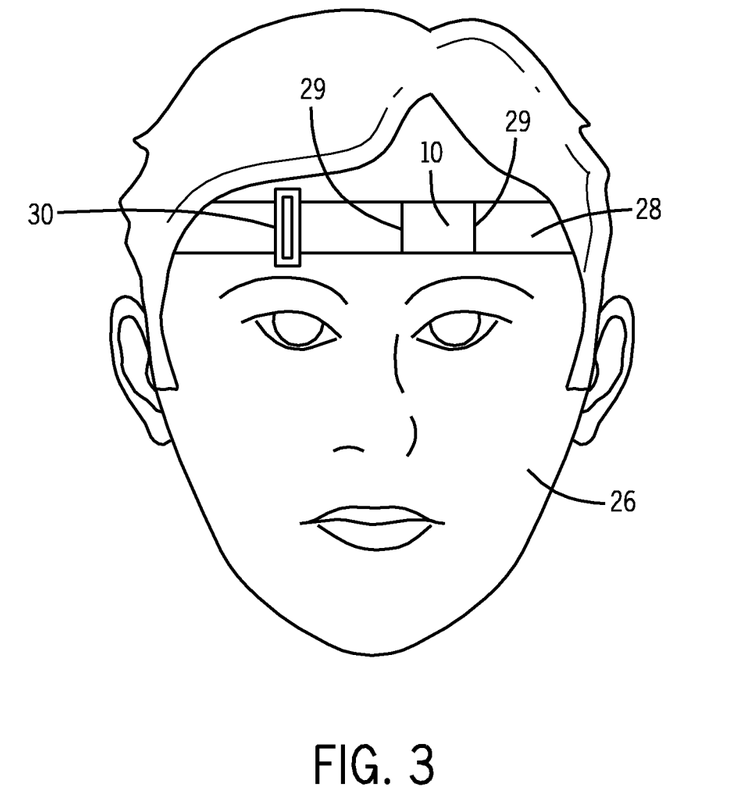
FIG. 3 is a depiction of a pulse oximetry patch of FIG. 1A or 1B disposed adjacent to the forehead of a patient in accordance with an embodiment.

Referring to FIG. 3, an embodiment of a pulse oximetry patch 10 may be held by a headband 28 adjacent to the forehead of a patient 26 above the left eye, for example. A typical headband 28 may be affixed to the pulse oximetry patch 10 along the edges 29 of the pulse oximetry patch 10. The headband 28 may be made of an elastic material configured to stretch to fit a wide range of head sizes. Additionally, the headband 28 may include a buckle 30 designed to adjust the fit of the headband 28. In alternate embodiments, the pulse oximetry patch 10 may be held in place with an external adhesive bandage (not shown). In fact, many techniques will be recognized by one of ordinary skill in the art for holding the pulse oximetry patch 10 against the skin of a patient, and the examples recited above should not be considered an exhaustive list of possible embodiments.

Figure 4:
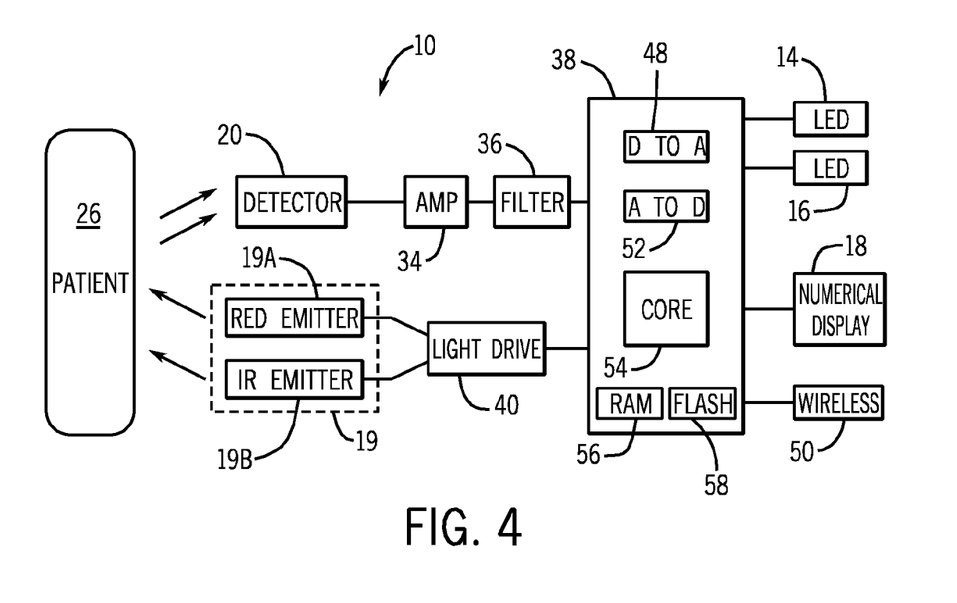
FIG. 4 is a block diagram of a pulse oximeter of FIG. 1A or 1B in accordance with an embodiment.

Turning now to FIG. 4, a block diagram of a pulse oximetry patch 10 is illustrated in accordance with an embodiment. It will be understood that an actual implementation may include more or fewer components as needed for a specific application. In this embodiment, the pulse oximetry patch 10 may include a red emitter 19A and an infra-red emitter 19B that are configured to transmit electromagnetic radiation through the tissue of a patient 26. In accordance with this embodiment, the emitters 19A and 19B may include an LED that emits electromagnetic radiation in the respective region of the electromagnetic spectrum. The emitted radiation transmitted from the emitters 19A and 19B into a patient's tissue is detected by the detector 20 after the radiation has passed through or reflected from blood perfused tissue of a patient 26. The detector 20 generates a photoelectrical signal correlative to the amount of radiation detected.

The signal generated by the detector 20 may then be amplified by an amplifier 34, filtered by a filter 36, and provided to one or more processor(s) 38. The processor(s) 38 may include an analog-to-digital converter 52 that converts the analog signal provided by the detector 20 into a digital signal. The analog-to-digital converter 52 may provide the digital signal to the core 54 to be processed for computing physiological parameters related to the patient 26. For example, the core 54 may compute a percent oxygen saturation of hemoglobin and/or a pulse rate, among other useful physiological parameters, as will be appreciated by one of ordinary skill in the art. By utilizing an analog-to-digital converter 52 within the processor(s) 38, the size and cost of the patch may be reduced, compared to traditional pulse oximeters that use a separate analog-to-digital converter. In presently contemplated embodiments, the processor(s) 38 may include a Mixed-Signal Microcontroller such as model number C8051F353 available from Silicon Laboratories.

In addition to computing physiological parameters, the processor(s) 38 may control the timing and intensity of the emitted electromagnetic radiation of the emitters 19A and 19B via a light drive circuit 40. In embodiments, the light drive circuit 40 may be driven by a digital-to-analog converter 48, included in the processor(s) 38. By utilizing a digital to analog converter 48 within the microprocessor 38, the size and cost of the patch may be reduced, compared to traditional pulse oximeters that use a separate digital-to-analog converter. In accordance with an embodiment, the light drive circuit 40 may have a low part count such as the light drive circuit discussed in detail in U.S. Provisional Patent Application No. 61/009,076, entitled "LED Drive Circuit and Method for Using Same." (TYHC:0008) which was filed Dec. 26, 2007, and is incorporated herein by reference in its entirety for all purposes. The reduced part count of the drive circuit 40 may further reduce the size, complexity, and cost of the pulse oximetry patch 10.

Furthermore, the processor(s) 38 may also include a RAM 56 and/or a flash memory 58 coupled to the core processor 54. The RAM 56 may be used to store intermediate values that are generated in the process of calculating patient parameters. The flash memory 58 may store certain software routines used in the operation of the patch 10, such as measurement algorithms, LED drive algorithms, and patient parameter calculation algorithms, for example. In certain embodiments, the patch 10 may include simplified pulse oximetry algorithms such that the computer code associated with those algorithms may be contained in the memory components of the processor(s) 38.

In some embodiments, the pulse oximetry patch 10 may also include other memory components that are not included in the processor(s) 38. For example, the patch 10 may include a read-only memory (ROM), which may be used to store such things as operating software for the patch 10 and algorithms for computing physiological parameters. In other embodiments, however, all of the processing memory and measurement software is included in the processor(s) 38.

Furthermore, in some embodiments, the patch 10 may also include a long-term memory device used for long-term storage of measured data such as measured physiological data or calculated patient parameters. In other embodiments, however, the cost and/or part count of the pulse oximetry patch 10 may be further reduced by eliminating any long-term storage of measured data. By eliminating long-term storage of measured data, smaller, less expensive memory components may be utilized, or, alternatively, some memory components may be eliminated. This may reduce the part count and the size and complexity of the pulse oximetry patch 10, compared to traditional pulse oximetry systems.

Also included in the pulse oximetry patch 10 is a display that may be coupled to the processor(s) 38 to allow for display of the computed physiological parameters. For example, the display may include an LED display 14, 16 operably coupled to the processor(s) 38 and programmed to operate as described above in relation to FIG. 1. For another example, the display may include a numerical display 18, such as a liquid crystal display, and drive circuitry configured to convert the processor 38 output into a format suitable for driving the numerical display 18.

Embodiments may also include a wireless device 50 configured to transmit computed patient parameters such as, for example, pulse rate, blood-oxygen saturation, or the raw data. The wireless device 50 may include any wireless technology known in the art. In an embodiment, the sensor 14 may transmit data via a wireless communication protocol such as WiFi, Bluetooth or ZigBee.

Figure 5:
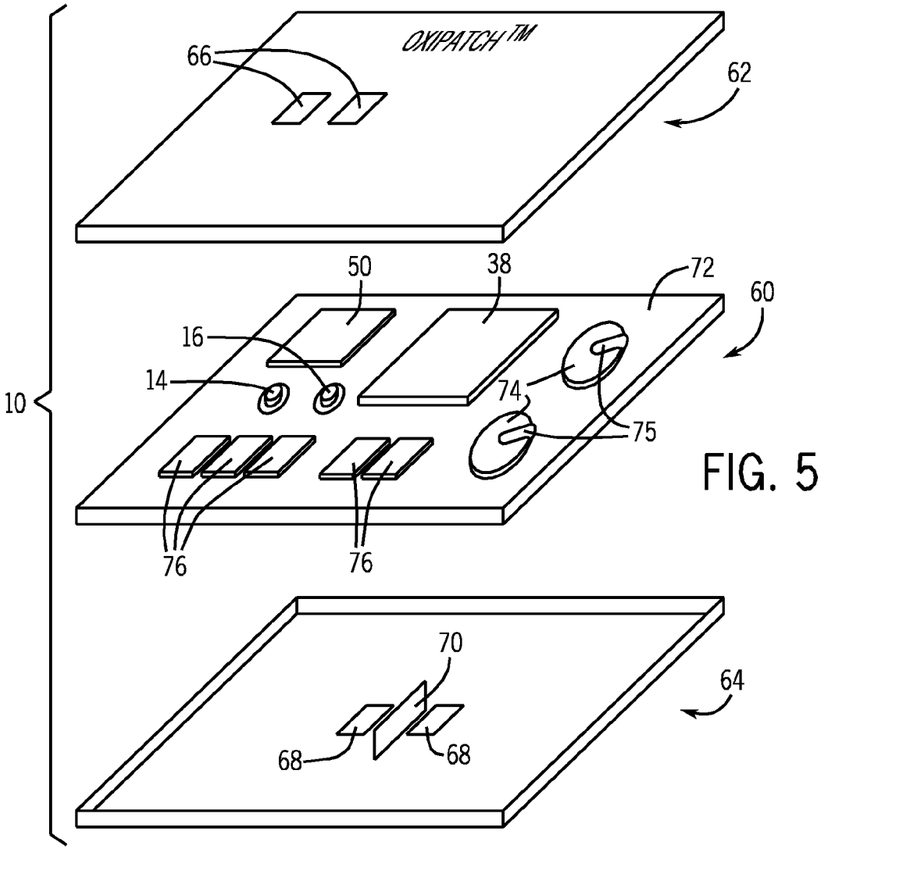
FIG. 5 is a perspective exploded view of the pulse oximeter of FIG. 1A in accordance with an embodiment.

Turning now to FIG. 5, an exploded view of a pulse oximetry patch 10 is shown. In some embodiments, the pulse oximetry patch 10 may include three layers: a middle layer 60, a top layer 62, and a bottom layer 64. The middle layer 60 may include all or substantially all of the circuitry of the pulse oximeter patch 10. To operably couple the various circuitries, the middle layer 60 may include a circuit board 72, which may be a flexible, or "flex," circuit board, and it may also be double sided. By making the circuit board 72 flexible, the pulse oximetry patch 10 can more easily conform to the contours of a patient while also preventing connection failures within the circuit board 72.

The circuit board 72 may include the microprocessor 38, as well as other circuit components 76, such as the circuit components discussed above with regard to FIGS. 4 and 5. The circuit board 72 may also include one or more batteries 74. The batteries 74 may be any small, lightweight battery such as a "coin cell" or "button cell." In some embodiments, the batteries 74 may be lithium ion batteries. In yet other embodiments, the batteries 74 may be nanowire batteries, i.e., high performance lithium ion batteries made from silicon nanowires. The batteries 74 serve to power the circuitry of the pulse oximetry patch 10 and are coupled to the circuitry through contacts 75.

In an embodiment, an electrically insulative film (not shown) may optionally be inserted between the batteries 74 and the contacts 75 during manufacture to prevent the pulse oximetry patch 10 from becoming activated prior to its intended use. In some embodiments, the electrically insulative film may be an extension of the protective sheet 24. For example, the protective sheet 24 may include an extension that is inserted during manufacture into the patch 10 through a small opening in the side of the patch 10. This extension may be disposed between a battery and its corresponding electrical contact to block the flow of current from the battery. In this way, removal of the protective sheet 24 would simultaneously expose the adhesive 22 and turn on the patch 10. In some embodiments, the removal of the electrically insulative film may be the only way of actuating the circuitry of the pulse oximetry patch 10.

In alternate embodiments, other means of activating the pulse oximetry patch 10 may be included. For example, the pulse oximetry patch 10 may include a power button or switch, or, alternatively, the pulse oximetry patch 10 may include a pressure sensitive button that may be enclosed in the patch 10 and operable through compression of the patch 10.

The circuit board 72 may also include the display LEDs 14 and 16. As stated above, the display LEDs 14 and 16 provide the caregiver with the patient's physiological data. As such, the display LEDs 14 and 16 align with the display windows 66, in the top layer 62. As discussed in relation to FIG. 1B, the middle layer may also include a numerical display 18, rather than a set of display LEDs.

In embodiments, the middle layer 60 may also include a wireless device 50 on the circuit board 72. As discussed above, the wireless device 50 may allow the pulse oximetry patch 10 to transmit data wirelessly to a remote monitor. As such, the wireless device 50 may include a wireless transmitter circuitry and a radio frequency antenna, such as, for example a microstrip or patch antenna.

Additionally, although not depicted, embodiments may include one or more pushbuttons coupled to the circuit board 72 of the middle layer 60. The pushbuttons may allow a user to turn the pulse oximetry patch 10 on or off or change a mode of the pulse oximetry patch 10. For example, a pushbutton may allow a caregiver to cycle through various physiological data displayed on the numerical display 18.

Furthermore, embodiments may also include an alarm and supporting circuitry. The alarm may be used as another way of communicating physiological data of a patient to a caregiver. For example, the alarm may be configured to emit a beeping sound corresponding with the heartbeat of a patient, or the alarm could be configured to sound when the patient's blood-oxygen saturation level falls below a certain acceptable level.

Figure 6:
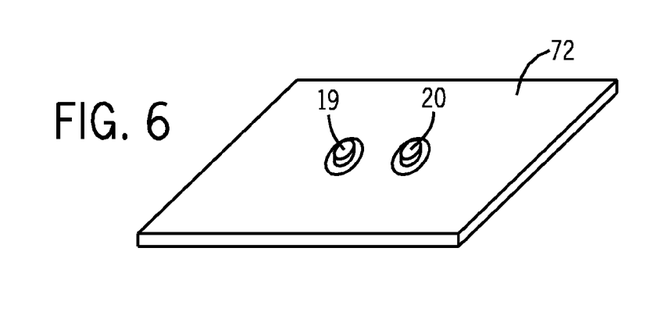
FIG. 6 is a perspective view of the back side of the pulse oximeter circuit board of FIG. 5 in accordance with an embodiment.

Turning briefly to FIG. 6, the back side of the circuit board 72 is shown. The back side of the circuit board 72 may include, at least, the emitter 19 and the detector 20. In embodiments, the emitter 19 includes a red LED and an infra-red LED. The emitter 19 and detector 20 are placed to align with the sensor window 68 in the bottom layer 64. In some embodiments, the bottom side of the circuit board 72 may include additional circuit components.

Returning to FIG. 5, the pulse oximetry patch 10 may include a top layer 62 and bottom layer 64 that enclose the middle layer 60 to protect the circuitry inside, thus forming a shell around the circuitry and the circuit board 72. The top layer 62 is the layer that is visible when disposed adjacent to the skin of a patient. As such, the top layer 62 may include display windows 66 that allow display components 14, 16, 18 to be seen through the top layer 62. The display windows 66 may be constructed in any manner that allows visible light to pass through the top layer 62. For example, the display windows 66 may include holes formed in the top layer 62. Furthermore, the display windows may include a translucent material configured to prevent fluids from entering the pulse oximetry patch 10 through the display windows 66. Alternatively, in some embodiments, the display windows 66 may include a reduced thickness of the top layer material, such that light may pass through the top layer 62 more easily at the display window 66.

The top layer 62 or the bottom layer 64 may also include a battery "door" for allowing access to the batteries 74. For example, part of the top layer 62 or the bottom layer 64 may swing or slide open to expose a battery compartment, allowing batteries to be changed. Alternatively, an embodiment may be configured such that the batteries are not accessible. As such, the pulse oximetry patch 10 would be intended to be thrown away after the batteries can no longer sufficiently charge the pulse oximetry device 10, which may be suitable for a disposable, one-use patch.

The top layer 62 and bottom layer 64 may be formed using any suitable material. In an embodiment, the top layer 62 and the bottom layer 64 may include a metal such as aluminum. In another embodiment, the top layer 62 and bottom layer 64 may include one or more polymers, such as, for example, silicon polymers, polyvinylchloride and polyolefins such as polyethylene. The polymers may be elastomeric to provide for flexibility of the pulse oximetry patch 10 such that it may conform to the tissue of a patient. Additionally, any number of ways for coupling the top layer 62 and the bottom layer 64 may be employed. For example, the layers may be glued, melted or snapped together at the edges.

In various embodiments, the middle layer 60 may be encased in a unitary outer shell through the use of injection overmolding. As will be appreciated by one of ordinary skill in the art, a typical injection overmolding technique will include placing one or more fully assembled middle layers 60 into a die and injecting a molten thermoplastic into the die to surround the middle layer 60. The mold may be constructed so that the display windows 66 and the sensor windows 68 are not obstructed. For example, the display LEDs 14 and 16, the emitter 19 and the detector 20 may be situated at an outer edge of the mold volume such that the molten thermoplastic will not completely cover these components.

In yet other embodiments, a clamshell style container may be formed in a sheet thermoforming method that will be understood by one of ordinary skill in the art. The clamshell container may then be folded over the middle layer 60 and sealed within the clamshell such as by melting, snapping or gluing the edges together.

In certain embodiments, the patch 10 may be configured so that the middle layer 60 can be easily removed for later recycling or reuse. In this embodiment, the top layer 62 and bottom layer 64 may be pulled apart without causing damage to the middle layer 60. The outer layers may then be discarded, while the middle layer 60 may be refitted with new batteries and repackaged with new top and bottom layers 62 and 64. This may allow a program of recycling to be implemented, in which customers return used pulse oximetry patches to the manufacturer, rather than discarding them. In this way, a manufacturer of the disclosed embodiment may be better able to conform to electronic waste regulations, such as those called for in the Waste Electrical and Electronic Equipment Directive recently legislated by the European Union.

Some embodiments of a pulse oximetry patch 10 may also include a disabling mechanism that prevents unauthorized manipulation or reuse of the patch 10. In this regard, the processor(s) 38 may be programmed to recognize whether the outer layers of the patch 10 have been separated. For example, a conductive contact may be included in the patch 10 that electrically couples an input/output (I/O) port of the processor(s) 38 to a zero-voltage reference. The I/O port may also be electrically coupled to a non-zero voltage through a high-resistance pull-up resistor. Furthermore, the conductive contact may be physically coupled to the top layer 62 and/or the bottom layer 64, such that separation of the layers will cause the conductive contact to open electrically, allowing the I/O port to float to the higher voltage level through the pull-up resistor. The processor(s) 38 may be configured such that detection of a non-zero voltage at the I/O port at start-up or during operation disables the patch 10.

Another example of a disabling mechanism may include an small integrated circuit (IC) chip such as an Erasable Programmable Read-Only Memory (EPROM) or a 1-Wire® chip available from Dallas Semiconductor Corp. The IC chip may be communicatively coupled to the processor(s) 38 and may hold information such as manufacturer information that may be read by the processor(s) 38. The processor(s) 38 may be programmed to read and verify the IC information as part of a start-up routine, for example. Furthermore, a contact may be electrically coupled to the IC and physically coupled to the upper layer 62 and/or lower layer 64 such that separation of the layers will cause the information stored on the IC to be erased, thereby disabling the patch 10. In this way, the information stored on the IC would have to be reprogrammed before the middle layer 60 could be reused.

What is claimed is:

1. A pulse oximetry patch adapted for placement adjacent to tissue to be tested, comprising:
    an upper layer comprising a display window;
    a bottom layer configured to be disposed on a tissue measurement site of a patient; and
    a middle layer disposed between the upper layer and the bottom layer comprising:
        one or more light emitters and one or more light detectors, the emitters and detectors configured to acquire physiological data from the patient;
        a drive engine configured to activate the one or more light emitters;
        an oximetry engine configured to receive a signal corresponding to the physiological data acquired by the detectors and generate an output corresponding to the physiological data; and
        a display adapted to receive the output corresponding to the physiological data; and
    wherein the upper layer and the bottom layer are configured to be separated from each other to enable the removal of the middle layer, and wherein the upper and bottom layers are disposable and the middle layer is reusable.

2. The pulse oximetry patch of claim 1, wherein the bottom layer comprises a layer of adhesive for attaching the pulse oximetry patch to the patient.

3. The pulse oximetry patch of claim 1, wherein the display comprises a display configured to display a numerical value.

4. The pulse oximetry patch of claim 1, wherein the display comprises one or more light emitting diodes.

5. The pulse oximetry patch of claim 4, wherein one of the one or more light emitting diodes blinks correlatively with the heartbeat of the patient.

6. The pulse oximetry patch of claim 4, wherein one of the one or more light emitting diodes is activated or deactivated in response to a comparison of a measured blood-oxygen saturation value and a programmed blood-oxygen saturation value.

7. The pulse oximetry patch of claim 6, wherein the one or more light emitting diodes are color coded.

8. The pulse oximetry patch of claim 1, comprising a wireless transmitter configured to transmit patient parameters to an external monitor, display, and/or other device.

9. The pulse oximetry patch of claim 1, wherein the drive engine, the oximetry engine, the display, or any combination thereof, are from a used pulse oximetry patch, and wherein the upper layer, the bottom layer, or a combination thereof, are new.

10. The pulse oximetry patch of claim 1, wherein the bottom layer comprises a window configured to align with the one or more light emitters and the one or more light detectors.

11. A pulse oximeter comprising:
    a single processor chip comprising:
        one or more first converters configured to activate one or more signal emitters for transmission of an emitted signal into tissue of a patient;
        one or more second converters configured to receive a signal generally correlative to the emitted signal from the tissue of the patient from one or more signal detectors;
        a core processor configured to calculate physiological parameters of the patient from the signal from the one or more signal detectors, wherein the core processor is configured to receive an additional signal and determine therefrom whether outer layers of the pulse oximeter have been separated from one another; and
        a program memory operatively coupled to the core processor and configured to store operating software of the pulse oximeter.

12. The pulse oximeter of claim 11, wherein the one or more first converters is configured to activate one or more display LEDs to indicate the physiological parameters of the patient.

13. The pulse oximeter of claim 11, wherein the single processor chip is configured to transmit output data corresponding with physiological parameters of the patient to a numerical display.

14. The pulse oximeter of claim 11, wherein the core processor is configured to disable the pulse oximeter in response to determining that the outer layers of the pulse oximeter have been separated from one another.

15. The pulse oximeter of claim 11, wherein the core processor is configured to erase the operating software stored in the program memory in response to determining that the outer layers of the pulse oximeter have been separated from one another.

16. The pulse oximeter of claim 15, wherein the program memory is configured to be reprogrammed with the operating software.

17. A method of remanufacturing a used pulse oximetry patch comprising:
    obtaining the used pulse oximetry patch, wherein the used pulse oximetry patch comprises:
        an upper layer comprising a display window;
        a bottom layer configured to be disposed on a tissue measurement site of a patient; and a middle layer disposed between the upper layer and the bottom layer comprising:
        one or more light emitters and one or more light detectors, wherein the emitters and detectors are configured to acquire physiological data from the patient;
        a light drive configured to activate the one or more light emitters;
        a processor configured to receive the physiological data from the detectors and to determine a physiological parameter of the patient based at least in part upon the physiological data; and
        a display configured to display the physiological parameter;
    retaining the middle layer in a remanufactured pulse oximetry patch; and replacing the upper layer, the bottom layer, or a combination thereof.

* * * * *